United States Patent
Akiyama

(10) Patent No.: US 10,307,534 B2
(45) Date of Patent: Jun. 4, 2019

(54) INFUSION SET AND CONNECTOR

(71) Applicant: TERUMO KABUSHIKI KAISHA, Tokyo (JP)

(72) Inventor: Kazuya Akiyama, Yamanashi (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 156 days.

(21) Appl. No.: 15/278,993

(22) Filed: Sep. 28, 2016

(65) Prior Publication Data
US 2017/0087298 A1 Mar. 30, 2017

(30) Foreign Application Priority Data

Sep. 29, 2015 (JP) .................................. 2015-190709

(51) Int. Cl.
| | | |
|---|---|---|
| *A61M 5/168* | (2006.01) | |
| *A61M 39/20* | (2006.01) | |
| *A61M 39/10* | (2006.01) | |
| *A61M 39/22* | (2006.01) | |

(52) U.S. Cl.
CPC .... *A61M 5/16804* (2013.01); *A61M 39/1011* (2013.01); *A61M 39/20* (2013.01); *A61M 39/22* (2013.01); *A61M 2039/1083* (2013.01); *A61M 2039/1088* (2013.01)

(58) Field of Classification Search
CPC .. A61M 2039/1083; A61M 2039/1088; A61M 39/10; A61M 39/1011; A61M 39/105; A61M 39/20; A61M 39/22; A61M 5/16804; A61M 5/16827; A61M 5/1408; A61M 5/1409; A61M 5/1413
See application file for complete search history.

(56) References Cited

U.S. PATENT DOCUMENTS

2006/0155249 A1* 7/2006 Hishikawa ............... A61M 5/14
604/252

FOREIGN PATENT DOCUMENTS

| JP | 2009-160452 A | 7/2009 | |
|---|---|---|---|
| JP | WO 2014049810 A1 * | 4/2014 | .......... A61M 39/045 |
| WO | WO-2014049810 A1 * | 4/2014 | .......... A61M 39/045 |

* cited by examiner

*Primary Examiner* — Kevin C Sirmons
*Assistant Examiner* — Tezita Z Watts
(74) *Attorney, Agent, or Firm* — Foley & Lardner LLP

(57) ABSTRACT

An infusion set includes a first infusion line set that forms a first infusion line with an injection port; and a connector including a male connector end that is insertable into the injection port, a female connector end to which a second infusion line can be connected, a flow channel, and a partition. The injection port and the connector are configured such that, when the male connector end of the connector is inserted into the injection port, the flow channel of the connector is divided by the partition into an in-flow channel configured to let in a liquid from the injection port in the first infusion line and an out-flow channel configured to let out the liquid that has entered the in-flow channel to the injection port.

7 Claims, 9 Drawing Sheets

INFUSION SET AND CONNECTOR

CROSS-REFERENCE TO RELATED APPLICATION

The present application claims priority to Japanese Application No. 2015-190709, filed on Sep. 29, 2015, the entirety of which is hereby incorporated by reference.

BACKGROUND

The present disclosure relates to an infusion set and a connector.

To administer infusion in a patient, a route for transporting liquid such as nutrients and medicinal fluids, i.e., an infusion line, must be set up. In general, an infusion line can be set up with infusion tubing, various medical devices, and connectors for interconnecting these different components. Some infusion sets that include infusion tubing, various medical devices, and connectors and that can form infusion lines are known.

When setting up an infusion line, a given infusion line can be provided with an injection port to which another infusion line is connected, so that several kinds of liquid such as medicinal fluid can be administered to a patient, for example. JP 2009-160452 A describes a setup of a system of infusion lines using a connector having: a male connector end having an axis; a first female connector end having an axis that is substantially parallel to the axis of the male connector end; and a second female connector end having an axis that is substantially orthogonal to the axis of the male connector end, in which system a port is always available on the connector for attaching another infusion line to an existing one.

SUMMARY

Patients' conditions can demand additional administration of different kinds of liquid such as medicinal fluid. For example, a patient can exhibit a sharp turn during surgery. In that case, an additional infusion line can be attached to an existing one through the first female connector end of the connector of the infusion set described in JP 2009-160452 A, because the first female connector end is always available as a port for attaching an additional infusion line. In this way, different kinds of liquid such as medicinal fluid to be administered can be readily increased because a necessary number of infusion lines are attachable without disconnecting existing infusion lines.

Unfortunately, however, with the method for attaching additional infusion lines described in JP 2009-160452 A, a liquid from an infusion line that is attached at a later time must travel a greater distance until it meets the main infusion line. Compared to a dose per unit time of a liquid from the main infusion line, a dose per unit time of a liquid infused from an additional infusion line can be as small as, for example, 1 mL to 5 mL per hour, depending on the patient's conditions and the kind of the medicinal fluid.

Thus, with the method for attaching additional infusion lines as described in JP 2009-160452 A, a liquid from an additional infusion line can take a longer time than expected until it meets the main infusion line, that is, until it is administered to a patient, depending on its dose per unit time or the route to a merge point in the main infusion line, which route can vary with the position of the additional infusion line relative to the main infusion line. In this respect, further improvement can be made for the infusion set disclosed in JP 2009-160452 A.

An object of certain embodiments of the present invention, therefore, is to provide an infusion set in which, even though a plurality of additional infusion lines are attached to a main infusion line, there are little differences between routes to the points to merge with the liquid in the main infusion line regardless of the positions of the additional infusion lines, and a connector that can be used in the infusion set.

An infusion set according to a first aspect of the present invention includes: a first infusion line set that forms a first infusion line with an injection port; and a connector having a male connector end that is insertable into the injection port, and a female connector end to which a second infusion line can be connected, wherein the connector further has a flow channel and a partition, wherein when the male connector end is inserted into the injection port, the flow channel of the connector is divided by the partition into an in-flow channel to let in a liquid through the injection port in the first infusion line and an out-flow channel to let out the liquid that has entered the in-flow channel to the injection port.

According to an embodiment of the present invention, the partition preferably divides at least an interior of the male connector end into the in-flow channel and the out-flow channel.

According to an embodiment of the present invention, when the female connector end is a first female connector end, the connector preferably further has a second female connector end, wherein the male connector end has a first central axis, the first female connector end has a second central axis, and the second female connector end has a third central axis, the first central axis being substantially in line with the third central axis while intersecting the second central axis, and the partition extends from the interior of the male connector end to an interior of the second female connector end, when a male connector end of an additional connector that is identical to the connector is inserted into the second female connector end, the partition adjoins a partition of the additional connector.

According to an embodiment of the present invention, the partition of the connector preferably includes a tip receiver and a protrusion that is protruded toward a tip of the second female connector end with respect to the tip receiver, wherein when the male connector end of the additional connector is inserted into the second female connector end, the tip receiver receives a tip of the male connector end of the additional connector while the protrusion is inside the male connector end of the additional connector in such a manner that the protrusion adjoins the partition of the additional connector.

The infusion set according to an embodiment of the present invention preferably further includes a cap to be attached to a tip portion of the male connector end to define vent channels for blocking liquid communication between the interior and an exterior of the male connector end, yet allowing gas communication between the interior and the exterior of the male connector end, wherein the cap has a protrusion configured to enter the male connector end through an opening at the tip of the male connector end and plug into one of the in-flow channel and the out-flow channel that is in communication with the first female connector end when the cap is attached to the tip portion of the male connector.

According to an embodiment of the present invention, when the connector is a first connector, and the partition of the connector is a first partition, the first infusion line set preferably has at least two infusion tubes and a second connector that is provided with the injection port and that interconnects the two infusion tubes, and the second connector preferably has a flow channel and a second partition, wherein when the male connector end of the first connector is inserted into the injection port, the flow channel of the second connector is divided by the second partition into an upstream flow channel that joins the in-flow channel and a downstream flow channel that joins the out-flow channel.

According to an embodiment of the present invention, the second partition preferably includes a tip receiver and a protrusion that is protruded toward a tip of the injection port with respect to the tip receiver, wherein when the male connector end of the first connector is inserted into the injection port, the tip receiver receives the tip of the male connector end of the first connector while the protrusion is inside the male connector end of the first connector in such a manner that the second partition adjoins the first partition.

A connector according to a second aspect of the present invention is a connector to be connected to an injection port disposed in a first infusion line, the connector including a flow channel defined therein, further including: a male connector end that can be inserted into the injection port; a female connector end to which a second infusion line can be connected; and a partition, wherein when the male connector end is inserted into the injection port, the flow channel is divided by the partition into an in-flow channel to let in a liquid through the injection port in the first infusion line and an out-flow channel to let out the liquid that has entered the in-flow channel to the injection port.

The connector according to an embodiment of the present invention preferably further includes a second female connector end into which a male connector end of an additional connector that is identical to the connector can be inserted, when the female connector end is a first female connector end, wherein when the male connector end of the additional connector is inserted into the second female connector end, the partition adjoins a partition of the additional connector.

An infusion set according to a third aspect of the present invention includes: the connector; and a second infusion line set that forms the second infusion line that can be connected to the first female connector end.

According to the present invention, an infusion set in which, even though a plurality of additional infusion lines are attached to a main infusion line, there are little differences between routes to the points to merge with the liquid in the main infusion line regardless of the positions of the additional infusion lines, and a connector that can be used in the infusion set, can be provided.

DETAILED DESCRIPTION

Figure 1:
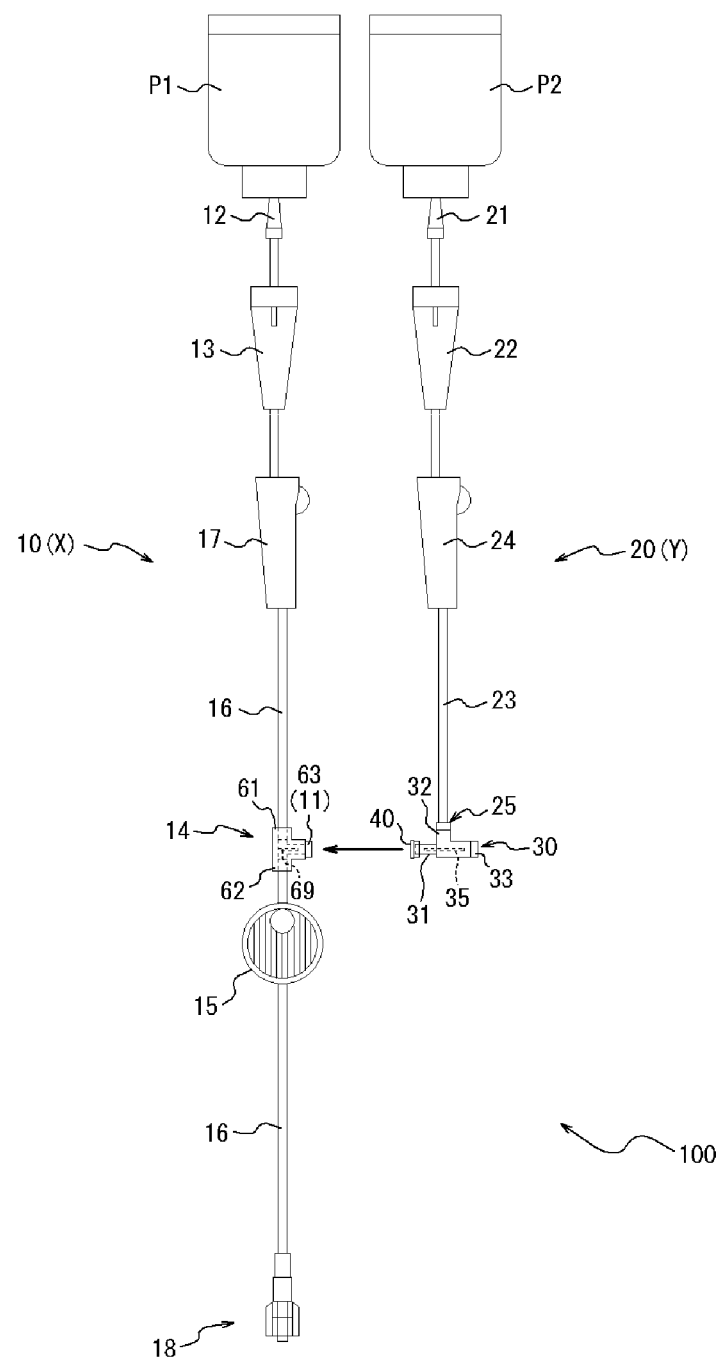
FIG. 1 shows an infusion set according to an embodiment of the invention.

Embodiments of the novel infusion set and connector will now be described with reference to FIGS. 1 through 9B. Like members and like parts in the drawings are given the same reference signs.

FIG. 1 shows an infusion set 100 according to one embodiment of the invention.

As shown in FIG. 1, the infusion set 100 includes: a first infusion line set 10 that forms a first infusion line X; a second infusion line set 20 that forms a second infusion line Y; a connector 30 that can interconnect the first infusion line X and the second infusion line Y; and a cap 40 attached to the connector 30. In FIG. 1, the connector 30 is detachably attached to an end of the second infusion line Y. Further in FIG. 1, the cap 40 is detachably attached to the connector 30.

The first infusion line X formed by the first infusion line set 10 is provided with an injection port 11 through which a liquid such as medicinal fluid can be injected into the first infusion line X.

The first infusion line set 10 according to the embodiment includes a spike 12 that is connectable to an infusion bag P1; a drip chamber 13 providing visual indication of the flow rate of a liquid from the infusion bag P1; a connector 14 provided with the injection port 11; a sterile filter 15; infusion tubes 16 (or infusion tubing 16, collectively) that can interconnect these components; and a roller clamp 17 with which the flow rate of the liquid passing through the infusion tubing 16 is controlled; the first infusion line X is formed by assembling these components.

For the purposes of discrimination and clarity in illustration, the connector 30 will be hereinafter called "first connector 30," while the connector 14 in the first infusion line set 10 will be hereinafter called "second connector 14."

A male lock connector 18 (manufactured to ISO594) is disposed at a downstream or distal end of the infusion tubing 16 of the first infusion line X according to the embodiment, so that the male lock connector 18 can be connected to an indwelling needle in a patient's body, a connector or extension tubing in another infusion line, or the like. Thus, if the spike 12 at an upstream or proximal end of the first infusion line X is connected to the infusion bag P1 on the one hand and the male lock connector 18 at the downstream or distal end of the first infusion line X is connected to the indwelling needle on the other hand, the liquid such as medicinal fluid in the infusion bag P1 can be transported down through the first infusion line X into the indwelling needle.

The second connector 14 interconnects two of the infusion tubes 16 in the first infusion line X. The injection port 11 of the second connector 14 allows another liquid, such as a medicinal fluid that is different from the one in the infusion bag P1 that is connected through the spike 12, to be injected into the first infusion line X.

The second infusion line Y formed by the second infusion line set 20 is an additional line to be attached to the first infusion line X. The second infusion line set 20 according to the embodiment includes a spike 21 that is connectable to an infusion bag P2; a drip chamber 22 providing visual indication of the flow rate of a liquid from the infusion bag; infusion tubes 23 (or infusion tubing 23, collectively); and a roller clamp 24 with which the flow rate of the liquid passing through the infusion tubing 23 is controlled; the second infusion line Y is formed by assembling these components.

A male connector 25 is disposed at a distal end of the infusion tubing 23 of the second infusion line Y so that the male connector 25 can be connected to a first female connector end 32 of the first connector 30 to be described later. Thus, if the spike 21 at a proximal end of the second infusion line Y is connected to the infusion bag P2 on the one hand and the male connector 25 at the distal end of the second infusion line Y is connected to the first female connector end 32 of the first connector 30 on the other hand (see FIG. 1), the liquid in the infusion bag P2 can be transported down through the second infusion line Y into the first connector 30.

The first connector 30 has a flow channel 34 defined therein, and is connectable to the injection port 11 in the first infusion line X. More specifically, the first connector 30 has a male connector end 31 insertable into the injection port 11 in the first infusion line X; a first female connector end 32 to which the second infusion line Y can be connected; and a second female connector end 33 into which a male connector end 31 of an additional connector that is identical to the first connector 30 is insertable. The second infusion line Y formed by the second infusion line set 20 can be attached to the first infusion line X formed by the first infusion line set 10 by means of the first connector 30.

A partition 35 is disposed in the first connector 30 to divide the flow channel 34 of the first connector 30 when the male connector end 31 is inserted into the injection port 11; the flow channel 34 is divided into an in-flow channel 34a to let in a liquid such as medicinal fluid through the injection port 11 in the first infusion line X and an out-flow channel 34b to let out the liquid that has entered the in-flow channel 34a to the injection port 11. When a male connector end 31 of an additional connector that is identical to the first connector 30 is inserted into the second female connector end 33 of the first connector 30, the partition 35 and a partition 35 of the additional connector are contiguous with each other. The relation between the partitions 35 of the interconnected first connectors 30 will be described later in detail (see FIG. 7).

The cap 40 can be attached to a tip portion of the male connector end 31 of the first connector 30 when priming is performed for the second infusion line Y to be attached to the first infusion line X, that is, the flow channel of the second infusion line Y is filled with liquid. More specifically, before connecting the second infusion line Y to the first infusion line X by the first connector 30, the male connector 25 at the distal end of the second infusion line Y is connected to the first female connector end 32 of the first connector 30 as shown in FIG. 1, and then the flow channel of the second infusion line Y and the flow channel 34 of the first connector 30 are primed (i.e., filled with liquid). As shown in FIG. 1, the cap 40 is attached to the tip portion of the male connector end 31 of the first connector 30 during priming.

The cap 40, attached to the tip portion 31b of the male connector end 31 during priming, cooperates with the male connector end 31 to define vent channels 41 for blocking liquid communication between the interior and the exterior of the male connector end 31 of the first connector 30, yet allowing gas communication between the interior and the exterior of the male connector end 31. The cap 40 will be described later in detail (see FIGS. 8A to 8C).

Although the first infusion line set 10 for the first infusion line X according to the embodiment includes the spike 12, the drip chamber 13, the second connector 14, the sterile filter 15, the infusion tubing 16, and the roller clamp 17, the first infusion line set 10 is not limited to this configuration but may have a different configuration as long as the first infusion line X has the injection port 11. The first infusion line set 10 may further include a medical device that is different from those listed in the preceding configuration, for example, a burette chamber or a one-touch clamp for closing the flow channel of the infusion tubing 16 at a predetermined site. Alternatively, the first infusion line set 10 may not include one or more of the components that were listed above. Furthermore, although the first infusion line set 10 according to the embodiment includes one second connector 14 that provides a single injection port 11, the first infusion line set 10 can include a plurality of connectors that are identical to the second connector 14 to provide the first infusion line X with a plurality of injection ports 11.

Although the second infusion line set 20 for the second infusion line Y according to the embodiment includes the spike 21, the drip chamber 22, the infusion tubing 23, and the roller clamp 24, the second infusion line set 20 is not limited to this configuration but may have a different configuration as long as the second infusion line Y is connectable to the first female connector end 32 of the first connector 30. The second infusion line set 20 may further include a medical device that is different from those listed in the preceding configuration, for example, a one-touch clamp for closing the flow channel of the infusion tubing 23 at a predetermined site. Alternatively, the second infusion line set 20 may not include one or more of the components that were listed above. Furthermore, the infusion tubing 23 may not be formed by a plurality of tubes but by a single tube. Furthermore, the above-listed components may be substituted by other medical devices that are intended to achieve the same purpose, for example, the spike 21 connectable to the infusion bag P2 may be substituted by a female lock connector (manufactured to ISO594) that can be connected to a syringe disposed at an end of the infusion tubing, containing a medicinal fluid or the like.

Figure 2:
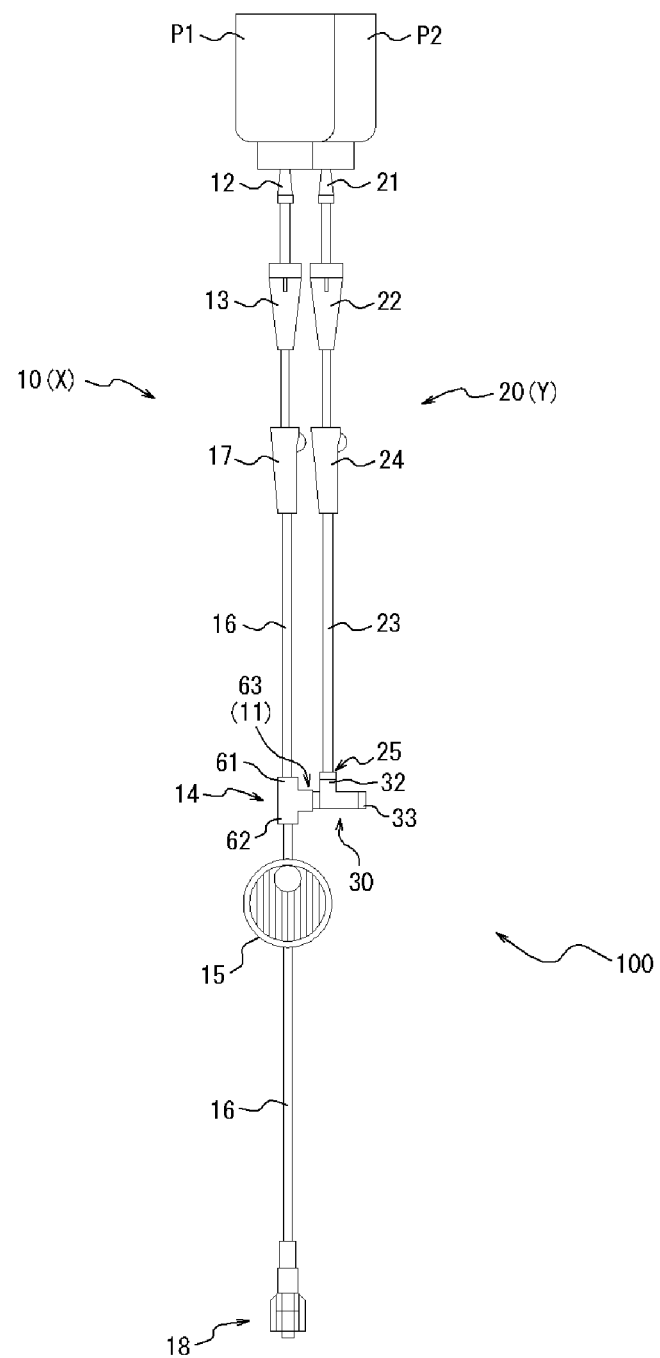
FIG. 2 shows an infusion line formed by interconnecting the infusion set shown in FIG. 1.

FIG. 2 shows the infusion set 100 in FIG. 1 in the form of a single infusion line after the first infusion line X and the second infusion line Y are interconnected by the first connector 30. In other words, the entire infusion line shown in FIG. 2 has been made by attaching the second infusion line Y to the first infusion line X by the first connector 30. Note that, in FIG. 2, the cap 40 has been detached from the male connector end 31 of the first connector 30 so that the male connector end 31 can be connected to the injection port 11 in the first infusion line X.

In the entire infusion line shown in FIG. 2, a liquid contained in the infusion bag P1 that is connected at the proximal end of the first infusion line X flows down through the tubing of the first infusion line X on the proximal side relative to the injection port 11, and when the liquid comes to the injection port 11, it enters the flow channel 34 of the first connector 30 through the injection port 11. The liquid flows through the flow channel 34 of the first connector 30, passes through the injection port 11 again to re-enter the flow channel of the first infusion line X, this time on the distal side relative to the injection port 11, and is administered to a patient through, for example, an indwelling needle at the distal end of the first infusion line X. This route, along which the liquid flows from the infusion bag P1 that is connected at the proximal end of the first infusion line X, is hereinafter called "main route."

In the infusion line shown in FIG. 2, a liquid contained in the infusion bag P2 that is connected at the proximal end of the second infusion line Y flows down the second infusion line Y into the flow channel 34 of the first connector 30 through the first female connector end 32, and merges with the above-described main route. Thus, the liquid from the infusion bag P2 as well as the liquid from the infusion bag P1 is administered to a patient through the indwelling needle or the like at the distal end of the first infusion line X. This route, along which a liquid from an infusion bag (the infusion bag P2 in the example shown in FIG. 2) at the proximal end of an additional line (the second infusion line Y in the example shown in FIG. 2) attached to the first infusion line X flows until the liquid merges with the main route, is hereinafter called "subsidiary route."

Hence, by connecting the first connector 30 to the injection port 11 in the first infusion line X, the main route, through which the liquid from the infusion bag P1 connected at the proximal end of the first infusion line X flows to the indwelling needle at the distal end of the first infusion line X, can be changed so that the flow channel 34 of the first connector 30 is included in the main route. In other words, the main route can be formed so that the liquid from the infusion bag P1 detours through the first connector 30 via the injection port 11.

Figure 3:
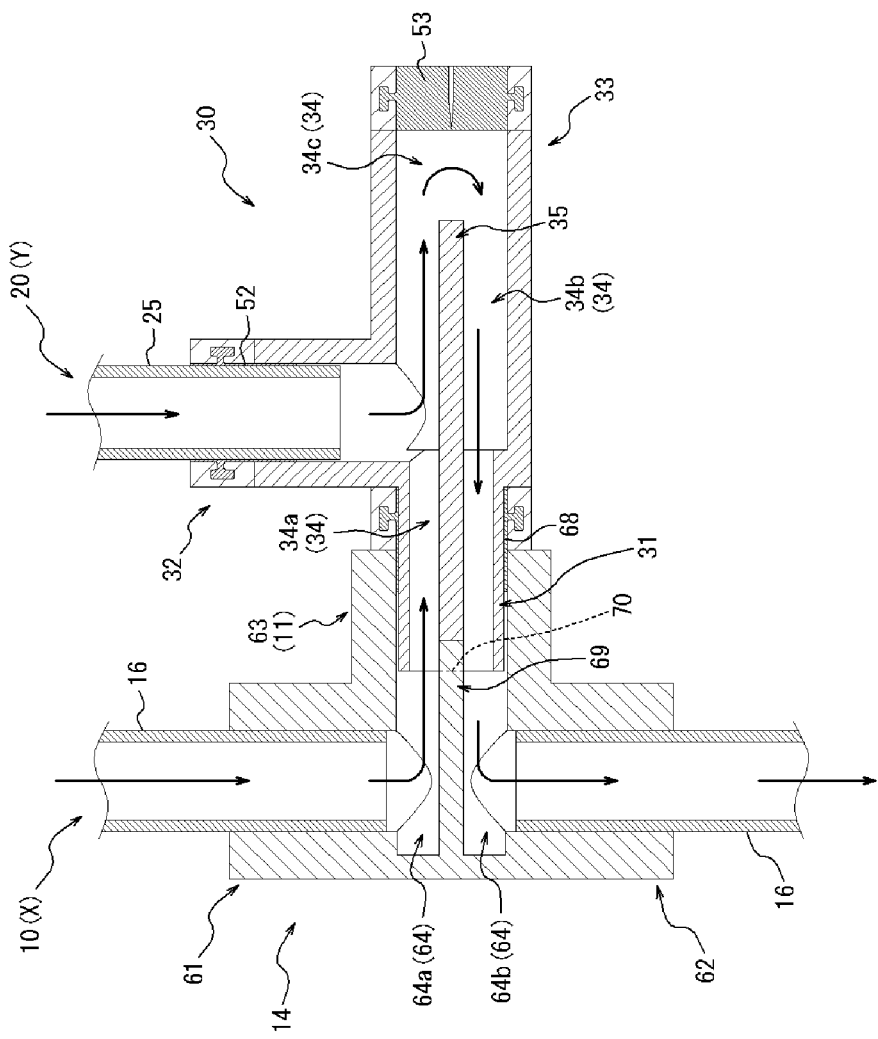
FIG. 3 is a cross-sectional view showing the vicinity of a first connector in the infusion line shown in FIG. 2.
Figure 4A:
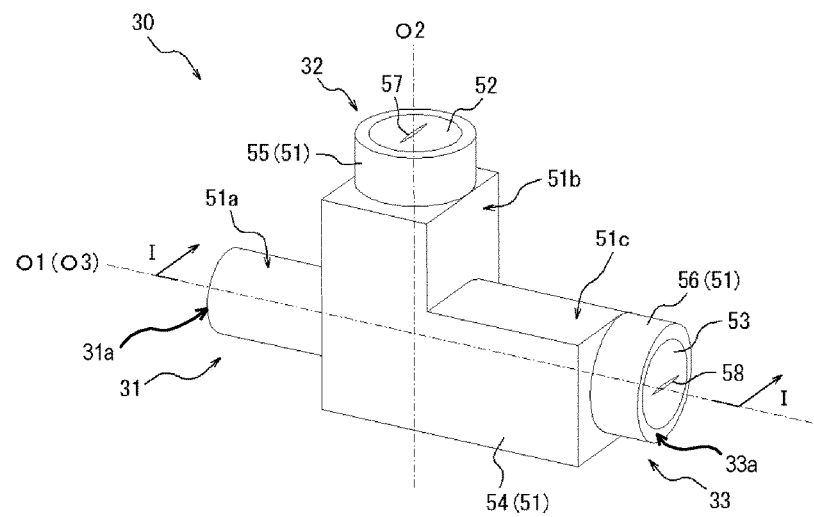
FIG. 4A is a perspective view showing the first connector alone.
Figure 4B:
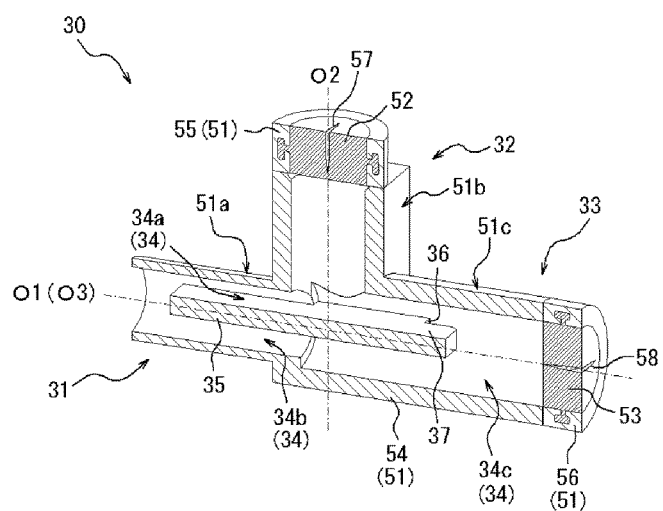
FIG. 4B is a cross-sectional perspective view taken along the I-I section in FIG. 4A.
Figure 5:
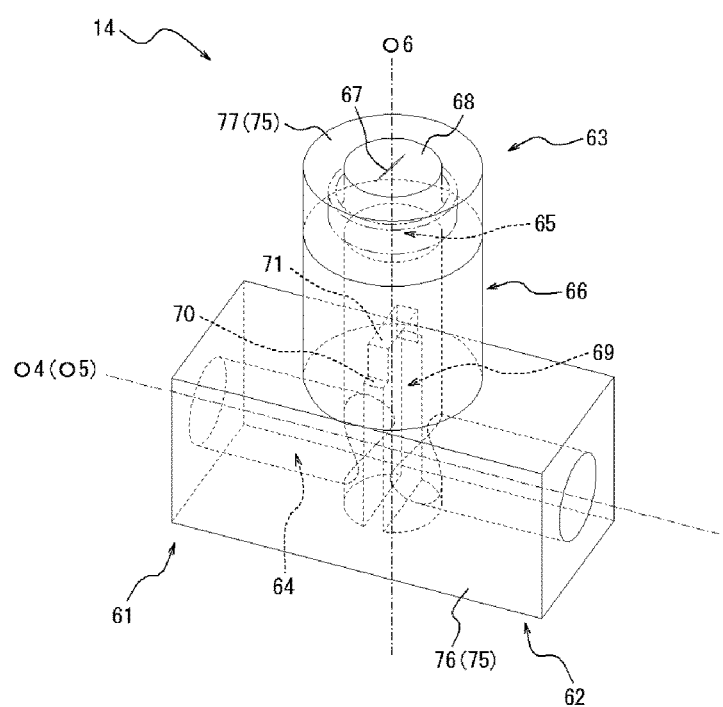
FIG. 5 is a perspective view showing a second connector alone.

Details of the first connector 30 and the second connector 14 and details of the merge point where the main route and the subsidiary route meet in the entire infusion line shown in FIG. 2, will now be described with reference to FIGS. 3 to 5. FIG. 3 is a cross-sectional view showing the vicinity of the first connector 30 in the entire infusion line shown in FIG. 2. FIG. 4A is a perspective view showing the first connector 30 alone; FIG. 4B is a cross-sectional perspective view taken along the I-I section in FIG. 4A. FIG. 5 is a perspective view showing the second connector 14 alone.

[First Connector 30]

As described above, the first connector 30 has the male connector end 31, the first female connector end 32, and the second female connector end 33. As shown in FIGS. 4A and 4B, the male connector end 31 has a central axis O1; the first female connector end 32 has a central axis O2; and the second female connector end 33 has a central axis O3; the central axis O1 and the central axis O3 are substantially in line with each other, while the central axis O2 does not run parallel to them but it runs across them. In this embodiment, the central axis O2 of the first female connector end 32 is substantially orthogonal to the central axis O1 of the male connector end 31 and the central axis O3 of the second female connector end 33.

The male connector end 31 can be liquid-tightly connected to a female connector end 63 (to be described later) of the second connector 14 as the injection port 11 in the first infusion line X.

The male connector end 31 can also be liquid-tightly connected to a second female connector end 33 of an additional connector that is identical to the first connector 30. That is, the male connector end 31 and the second female connector end 33 enable a plurality of first connectors 30 to be connected in series along the central axes O1 and O3. The configuration in which the first connectors 30 are interconnected in series will be described later in detail (see FIG. 7).

The first female connector end 32 can be liquid-tightly connected to the male connector 25 at the distal end of the second infusion line Y.

Thus, the first connector 30 can liquid-tightly connect the second infusion line Y to the first infusion line X.

As described above, the partition 35 is disposed in the first connector 30 for dividing the flow channel 34 into the in-flow channel 34a and the out-flow channel 34b. As shown in FIG. 3 and FIGS. 4A and 4B, the partition 35 according to the embodiment divides at least the interior of the male connector end 31 into the in-flow channel 34a and the out-flow channel 34b. Thus, when the male connector end 31 of the first connector 30 is inserted into the female connector end 63 of the second connector 14 as the injection port 11 in the first infusion line X, the in-flow channel 34a and the out-flow channel 34b join the flow channel of the first infusion line X, whereby the main route that includes the flow channel 34 of the first connector 30 as a detour, as described above, is established.

The partition 35 according to the embodiment extends from the interior of the male connector end 31 to the interior of the second female connector end 33. Hence, when a male connector end 31 of an additional connector that is identical to the first connector 30 is inserted into the second female connector end 33, the partitions 35 of the connectors contiguously adjoin each other. The relation between the partitions 35 of the interconnected first connectors 30 will be described later (see FIG. 7).

The first connector 30 according to the embodiment has a housing 51, a first elastic valve 52, and a second elastic valve 53, in which the housing 51 according to the embodiment includes a holder 54, a cap member 55 that is supported by the holder 54 and that holds the first elastic valve 52; and a cap member 56 that is supported by the holder 54 and that holds the second elastic valve 53. The above-described male connector end 31 is formed by a tubular first cylinder 51a of the holder 54 of the housing 51. The above-described first female connector end 32 is formed by: a second cylinder 51b that is formed by the holder 54 and the cap member 55 of the housing 51; and the first elastic valve 52 that seals the second cylinder 51b and that is provided with a slit 57. The above-described second female connector end 33 is formed by: a third cylinder 51c that is formed by the holder 54 and the cap member 56 of the housing 51; and the second elastic valve 53 that seals the third cylinder 51c and that is provided with a slit 58.

The flow channel of the first connector 30 is defined by the holder 54 of the housing 51 because the partition 35, as described above, is integral to the holder 54. The partition 35 according to the embodiment, as shown in FIG. 4B, is a planar partition, having a thickness along the central axis O2 of the first female connector end 32, and extending along the central axes O1 and O3 from the interior of the male connector end 31 to the interior of the second female connector end 33. The partition 35 according to the embodiment has a tip receiver 36 and a protrusion 37 that is protruded toward the tip 33a of the second female connector end 33 with respect to the tip receiver 36; when a male connector end 31 of an additional connector that is identical to the first connector 30 is inserted into the second female connector end 33, the tip receiver 36 receives the tip of the inserted male connector end 31. Details of the tip receiver 36 and the protrusion 37 will be provided when a configuration in which the first connectors 30 are interconnected in series is discussed in a later section (see FIG. 7).

As shown in FIG. 4B, the partition 35 does not contact the second elastic valve 53 of the second female connector end 33 so that a connecting channel 34c that interconnects the in-flow channel 34a and the out-flow channel 34b, as described above, is formed between the partition 35 and the second elastic valve 53 along the central axis O3 of the second female connector end 33.

The cap member 55 and the cap member 56 are securely joined to the holder 54 by ultrasonic welding or the like, or they may be formed integrally to the holder 54. Alternatively, the cap member 55 may be formed by two members, a lower cap holding the first elastic valve 52 and an upper cap; the cap member 56 may also be formed by two members, a lower cap holding the second elastic valve 53 and an upper cap.

[Second Connector 14]

As shown in FIG. 5, the second connector 14 includes an upstream port 61 to which the infusion tubing 16 (see FIG. 1, for example) on the proximal side relative to the second connector 14 in the first infusion line X is connected; a downstream port 62 to which the infusion tubing 16 on the distal side relative to the second connector 14 in the first infusion line X is connected; and a female connector end 63 as the injection port 11 through which a liquid such as medicinal fluid can be injected into the first infusion line X. Inside the second connector 14, a flow channel 64 is defined, communicating the interior of the upstream port 61 with the interior of the downstream port 62.

The upstream port 61 and the downstream port 62 may have any configuration that enables liquid-tight connection to the flow channel of the infusion tubing 16, that is, ends of the infusion tubing 16 may be inserted into the upstream port 61 and the downstream port 62, respectively, as shown in FIG. 3, or may be fit over outer walls of the upstream port 61 and the downstream port 62, respectively. Furthermore, the upstream port 61 may be a female lock connector (manufactured to ISO594) and the end of the infusion tubing 16 to be connected to the upstream port 61 may have a male lock connector (manufactured to ISO594); these female and male lock connectors may be connected to each other so that the upstream port 61 and the infusion tubing 16 are interconnected. Likewise, the downstream port 62 may be a male lock connector (manufactured to ISO594) and the end of the infusion tubing 16 to be connected to the downstream port 62 may have a female lock connector (manufactured to ISO594); these female and male lock connectors may be connected to each other so that the downstream port 62 and the infusion tubing 16 are interconnected.

To prevent dislocation of the infusion tubing 16 from the upstream port 61, the infusion tubing 16 may be fixed to the upstream port 61 by ultrasonic welding or the like. The same is true for the downstream port 62 and the infusion tubing 16 attached to the downstream port 62.

The female connector end 63 includes a tubular cylinder 66 that defines an insert port 65 into which the male connector end 31 of the first connector 30 can be inserted; and an elastic valve 68 that seals the insert port 65 and that is provided with a slit 67. The insert port 65 herein refers to a space in which the elastic valve 68 is located, and the insert port 65 communicates with the flow channel 64 below the elastic valve 68.

The second connector 14 according to the embodiment has a substantially T-shape profile as shown in FIG. 5. More specifically, the upstream port 61 has a central axis O4 and the downstream port 62 has a central axis O5, the central axes O4 and O5 being substantially in line with each other, that is, the upstream port 61 and the downstream port 62 are aligned substantially linearly. The female connector end 63 has a central axis O6 that runs substantially orthogonal to the central axis O4 of the upstream port 61 and the central axis O5 of the downstream port 62. Because the second connector 14 according to the embodiment has such a shape, it is provided with a partition 69 therewithin. If a liquid flows into the second connector 14 through the upstream port 61 when the female connector end 63 is not connected to another medical device like the first connector 30, the partition 69 makes the liquid make a detour in the female connector end 63 before the liquid flows out from the second connector 14 through the downstream port 62.

More specifically, the partition 69 is a planar partition having a thickness along the central axis O4 of the upstream port 61 and the central axis O5 of the downstream port 62, and extending orthogonal to the central axes O4 and O5. The partition 69 divides between the upstream port 61 and the downstream port 62, extending into the interior of the female connector end 63. The partition 69 does not contact the elastic valve 68 of the female connector end 63, allowing a gap to exist between the partition 69 and the elastic valve 68 along the central axis O6 of the female connector end 63. In this way, a liquid that has flown into the flow channel 64 of the second connector 14 through the upstream port 61 flows through an upstream side of the partition 69 (the left hand side of the partition 69 in the FIG. 5) along the partition 69 toward the tip of the female connector end 63, passes through the gap between the partition 69 and the elastic valve 68, flows through a downstream side of the partition 69 (the right hand side of the partition 69 in the FIG. 5) proximally in the female connector end 63, and flows out of the second connector 14 through the downstream port 62. The partition 69 thus prevents a medicinal fluid or the like from getting stalled in the female connector end 63.

Thus, a liquid that has flown into the second connector 14 through the upstream port 61 in the first infusion line X (see FIG. 1) flows through the female connector end 63, flows out of the second connector 14 through the downstream port 62, and is transported to the distal end of the first infusion line X.

For the purposes of discrimination and clarity in illustration, the partition 35 of the first connector 30 will be hereinafter called "first partition 35," while the partition 69 of the second connector 14 will be hereinafter called "second partition 69."

When the male connector end 31 of the first connector 30 is inserted into the female connector end 63 as the injection port 11, the second partition 69 cooperates with the first partition 35 to divide the flow channel 64 of the second connector 14 into an upstream flow channel 64a that joins the in-flow channel 34a and a downstream flow channel 64b that joins the out-flow channel 34b (see FIG. 3). Details of this configuration will be described later.

As shown in FIG. 5, the second partition 69 includes a tip receiver 70 that receives the tip 31a of the male connector end 31 of the first connector 30 when the male connector end 31 is inserted into the female connector end 63; and a protrusion 71 that protrudes toward the tip of the female connector end 63 with respect to the tip receiver 70. When the tip receiver 70 receives the tip 31a of the male connector end 31 of the first connector 30, the protrusion 71 is inside the male connector end 31 of the first connector 30, abutting against the first partition 35 of the first connector 30, whereby the second partition 69 is contiguous with the first partition 35. The relation between the male connector end 31 of the first connector 30 and the tip receiver 70 and protrusion 71 will be described later (see FIG. 3).

The second connector 14 according to the embodiment has a housing 75 and the elastic valve 68 fixed to the housing 75. The housing 75 has a holder 76 and a cap member 77 that is supported by the holder 76 and that holds the elastic valve 68. The upstream port 61 and the downstream port 62, as described above, are formed by the holder 76 of the housing 75. The above-described cylinder 66 of the female connector end 63 is formed by the holder 76 and the cap member 77 of the housing 75. The above-described second partition 69 is integral to the holder 76. Although the housing 75 according to the embodiment has the holder 76 and the cap member 77 that is secured to the holder 76 by ultrasonic welding or the like, the holder 76 and the cap member 77 may be made as an integral member. Alternatively, the holder 76 and the cap member 77 may be individually made from two or more members; for example, the cap member 77 may be formed by a lower cap holding the elastic valve 68 and an upper cap.

[Connecting First Connector 30 to Second Connector 14]

The above-described first connector 30 is liquid-tightly connected to the second connector 14 by inserting the male connector end 31 of the first connector 30 into the female connector end 63 of the second connector 14.

When the male connector end 31 is inserted into the female connector end 63, a tip end face at the tip 31a of the male connector end 31 abuts against the tip receiver 70 of the second partition 69, whereby an insertion depth of the male connector end 31 with respect to the female connector end 63 is restrained. More specifically, the second partition 69 has the protrusion 71 that protrudes toward the tip of the female connector end 63, and there is defined a clearance between the protrusion 71 and an inner peripheral surface of the female connector end 63. When the male connector end 31 is inserted into the female connector end 63, a peripheral wall at the tip 31a of the male connector end 31 enters the clearance, and the tip end face of the male connector end 31 abuts against the tip receiver 70 of the second partition 69. In other words, the tip receiver 70, the protrusion 71, and the inner peripheral surface of the female connector end 63 together define a recess, where the tip receiver 70 serves as a bottom. When the peripheral wall at the tip 31a of the male connector end 31 enters this recess and the tip end face of the male connector end 31 abuts against the tip receiver 70, the male connector end 31 is blocked from being further advanced in the female connector end 63.

The recess, i.e., the above-described clearance, has a width from the protrusion 71 of the second partition 69 to the inner peripheral surface of the female connector end 63, which width is substantially equal to or slightly smaller than the thickness of the peripheral wall at the tip 31a of the male connector end 31. Thus, when the tip end face of the male connector end 31 abuts against the tip receiver 70, an inner surface and an outer surface of the peripheral wall at the tip 31a of the male connector end 31 are in contact with a side surface of the protrusion 71 of the second partition 69 and the inner peripheral surface of the female connector end 63, respectively, that is to say, the peripheral wall at the tip 31a of the male connector end 31 is disposed between the side surface of the protrusion 71 of the second partition 69 and the inner peripheral surface of the female connector end 63.

Furthermore, when the tip end face of the male connector end 31 abuts against the tip receiver 70, the protrusion 71 of the second partition 69 is inside the male connector end 31 through an opening at the tip 31a of the male connector end 31, and a tip end face of the protrusion 71 abuts against a tip end face of the first partition 35 in the male connector end 31. Here, when the tip end face of the male connector end 31 abuts against the tip receiver 70, the entire tip end face of the protrusion 71 abuts against the entire tip end face of the first partition 35.

Hence, as a result of insertion of the male connector end 31 into the female connector end 63, the first partition 35 and the second partition 69 can be arranged contiguously. In other words, as shown in FIG. 3, when the male connector end 31 is inserted into the female connector end 63, the second partition 69 contiguously abuts against the first partition 35, thereby dividing the flow channel 64 of the second connector 14 into the upstream flow channel 64a that joins the in-flow channel 34a of the first connector 30 and the downstream flow channel 64b that joins the out-flow channel 34b of the first connector 30.

Thus, when the male connector end 31 of the first connector 30 is not inserted into the female connector end 63, there exists the gap between the second partition 69 and the elastic valve 68 in the second connector 14, as described above, allowing the flow channel 64 to communicate between the upstream side and the downstream side of the second partition 69. Once the male connector end 31 is inserted into the female connector end 63, the first partition 35 and the second partition 69 abut against each other, providing a contiguously combined partition. Consequently, the upstream side and the downstream side of the flow channel 64 of the second connector 14 are no longer in communication within the second connector 14, but the flow channel 64 of the second connector 14 is now completely divided by the second partition 69 into the upstream flow channel 64a that joins the in-flow channel 34a of the first connector 30 and the downstream flow channel 64b that joins the out-flow channel 34b of the first connector 30 (see FIG. 3).

[Merge Point of Main Route and Subsidiary Route]

When the male connector end 31 of the first connector 30 is inserted into the female connector end 63 of the second connector 14 as the injection port 11 in the first infusion line X so that the combined partition is made by the first partition 35 and the second partition 69, the liquid from the infusion bag P1 connected at the proximal end of the first infusion line X (see FIGS. 1 and 2) flows through the upstream flow channel 64a of the second connector 14, the in-flow channel 34a of the first connector 30, the connecting channel 34c of the first connector 30, the out-flow channel 34b of the first connector 30, and the downstream flow channel 64b of the second connector 14, in the described order (see the arrows in FIG. 3).

That is, as a result of connecting the male connector end 31 of the first connector 30 to the female connector end 63 as the injection port 11, the main route can be formed for the liquid from the infusion bag P1 to make a detour in the first connector 30 via the female connector end 63.

Further, as shown in FIG. 3, the male connector 25 at the distal end of the second infusion line Y is connected to the first female connector end 32 of the first connector 30, so that the liquid from the infusion bag P2 flowing through the second infusion line Y (see FIGS. 1 and 2) can enter the in-flow channel 34a through the first female connector end 32, that is, the liquid can merge into the main route.

In this embodiment, as shown in FIG. 3, the tip 31a of the male connector end 31 completely penetrates the slit 67 (see FIG. 5) of the elastic valve 68 of the female connector end 63, with the tip end face of the male connector end 31 abutting against the tip receiver 70. With the tip end face of the male connector end 31 abutting against the tip receiver 70, the first partition 35 of the first connector 30 and the second partition 69 of the second connector 14 abut against each other so that the first partition 35 and the second partition 69 form a combined partition.

Figure 9A:
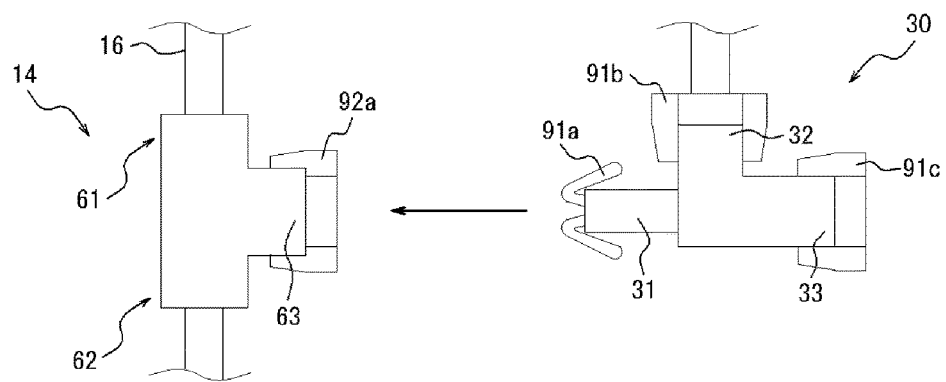
FIGS. 9A and 9B show an exemplary lock mechanism.
Figure 9B:
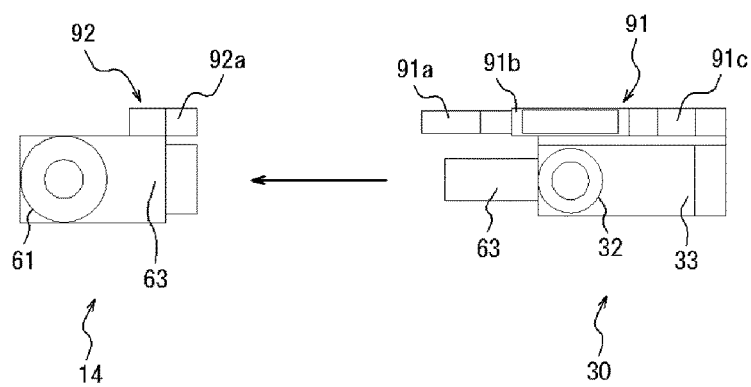

The first connector 30 and the second connector 14 are preferably provided with a lock mechanism for securing circumferential positions of the male connector end 31 and the female connector end 63 relative to each other when the male connector end 31 is being connected to the female connector end 63. FIGS. 9A and 9B show an exemplary lock mechanism. FIG. 9A shows side views of the first connector 30 and the second connector 14; FIG. 9B shows front views of the first connector 30 seen from the tip end face of the first female connector end 32 and the second connector 14 seen from the tip end face of the upstream port 61.

In FIGS. 9A and 9B, the first connector 30 has a first lock 91 and the second connector 14 has a second lock 92. The lock mechanism shown in FIGS. 9A and 9B is formed by the first lock 91 and the second lock 92. The first lock 91 has a lock nail 91a disposed adjacent to the male connector end 31, a first nail receiver 91b disposed adjacent to the first female connector end 32, and a second nail receiver 91c disposed adjacent to the second female connector end 33. The second lock 92 has a nail receiver 92a disposed adjacent to the female connector end 63 for engaging with the lock nail 91a to secure the position of the second connector 14 with respect to the first connector 30.

The first nail receiver 91b and the second nail receiver 91c have the same configuration as the nail receiver 92a of the second lock 92.

The lock nail 91a enters an opening of the nail receiver 92a when the male connector end 31 is being inserted into the female connector end 63 (see the arrows in FIGS. 9A and 9B), and engages with the nail receiver 92a by getting lodged against an inner wall of the opening. Once the lock nail 91a engages with the nail receiver 92a, the position of the second connector 14 with respect to the first connector 30 is secured. In the examples shown in FIGS. 9A and 9B, the position of the second connector 14 with respect to the first connector 30 is secured along the axis and circumference of the male connector end 31.

The lock nail 91a is of a type that it can engage with the nail receiver 92a only when the male connector end 31 and the female connector end 63 are at predetermined circumferential positions with respect to each other; if the male connector end 31 and the female connector end 63 are off the predetermined circumferential positions, the lock nail 91a fails to engage with the nail receiver 92a. Thus, because the lock nail 91a and the nail receiver 92a require circumferential positioning for engagement, the first partition 35 and the second partition 69 can appropriately abut against each other to form a combined partition.

When a male connector end 31 of an additional connector that is identical to the first connector 30 is connected to the second female connector end 33 of the first connector 30, a lock nail 91a of the additional connector engages with the second nail receiver 91c of the first connector 30 in the same way as in the case of the engagement between the lock nail 91a and the nail receiver 92a as described above. In this way, when a plurality of first connectors 30 are interconnected in series, the first partitions 35 of the first connectors 30 adjoin each other at suitable positions.

The lock mechanism is not limited to the configurations shown in FIGS. 9A and 9B, but may have any configuration as long as the male connector end 31 and the female connector end 63 can be circumferentially positioned and the position of the second connector 14 can be secured with respect to the first connector 30. Thus, a lock mechanism preferably has a lock element such as a lock nail disposed on one of the first connector 30 and the second connector 14, and a receiving element such as a nail receiver disposed on the other of the first connector 30 and the second connector 14; the receiving element is engaged with the lock element while the receiving element is at a predetermined position with respect to the lock element along the circumference of the male connector end 31, whereby the position of the one of the first connector 30 and the second connector 14 is secured with respect to the other of the first connector 30 and the second connector 14. Furthermore, the lock mechanism preferably has an unlock mechanism.

[Attaching Additional Infusion Lines to First Infusion Line X]

The infusion set 100 has been described, in which the first infusion line X and the second infusion line Y are connected by the first connector 30. Next, a configuration in which multiple additional infusion lines are attached to the first infusion line X by multiple first connectors 30 will be described.

Figure 6:
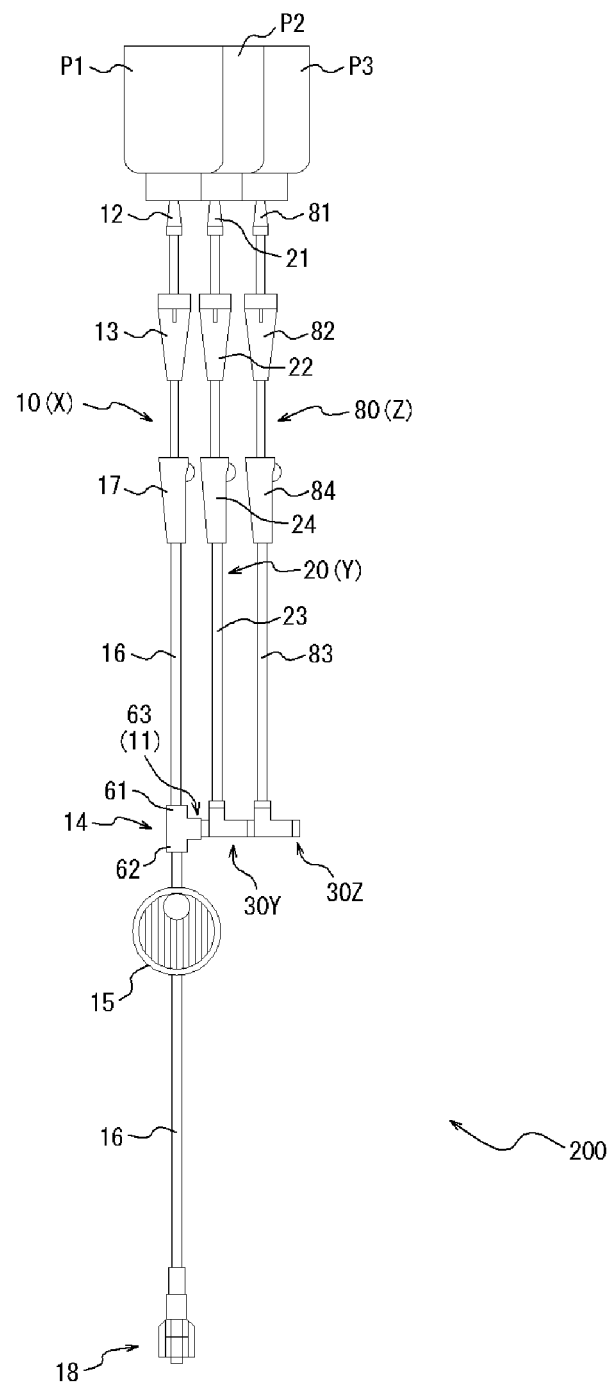
FIG. 6 shows an infusion set according to an embodiment of the invention.
Figure 7:
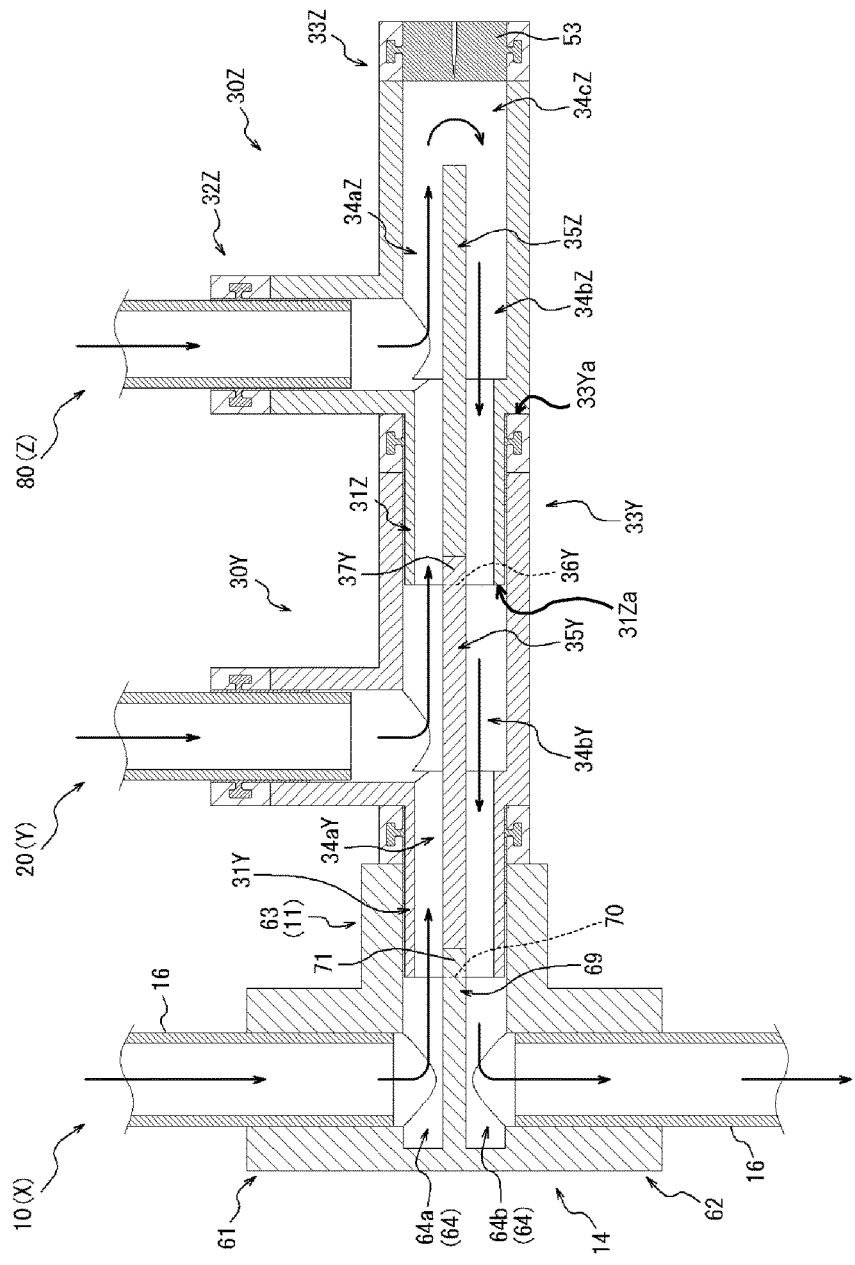
FIG. 7 is a cross-sectional view showing the vicinity of first connectors in the infusion lines shown in FIG. 6.

FIG. 6 shows an infusion set 200, in which a third infusion line Z as an additional infusion line has been attached to the infusion line shown in FIG. 2. FIG. 7 is a cross-sectional view showing the vicinity of the first connectors 30 in the infusion lines shown in FIG. 6, where a main route and subsidiary routes meet. The infusion set 200 will now be described with reference to FIGS. 6 and 7.

The infusion set 200 includes a first infusion line set 10 that forms a first infusion line X; a second infusion line set 20 that forms a second infusion line Y; a third infusion line set 80 that forms the third infusion line Z; and two first connectors 30 that can connect the second infusion line Y and the third infusion line Z to the first infusion line X, respectively. The details of the first infusion line set 10, the second infusion line set 20, and the first connector 30 are as described above; therefore, they will not be described further.

The third infusion line set 80 shown in FIG. 6 has similar components as the second infusion line set 20, which are: a spike 81 that is connectable to an infusion bag P3; a drip chamber 82 providing visual indication of the flow rate of a liquid from the infusion bag; infusion tubes 83 (or infusion tubing 83, collectively); and a roller clamp 84 with which the flow rate of the liquid passing through the infusion tubing 83 is controlled; the third infusion line Z is formed by assembling these components.

Nevertheless, the third infusion line set 80 that forms the third infusion line Z is not limited to the above configuration but may have any configuration as long as the third infusion line Z can be connected to the first female connector end 32 of the first connector 30. The third infusion line set 80 may further include a medical device that is different from those listed in the preceding configuration, for example, a one-touch clamp for closing the flow channel of the infusion tubing 83 at a predetermined site. Alternatively, the third infusion line set 80 may not include one or more of the components that were listed above. Furthermore, the infusion tubing 83 may not be formed by a plurality of tubes but by a single tube. Furthermore, the above-listed components may be substituted by other medical devices that are intended to achieve the same purpose, for example, the spike 81 connectable to the infusion bag P3 may be substituted by a female lock connector (manufactured to ISO594) that can be connected to a syringe disposed at an end of the infusion tubing, containing a medicinal fluid or the like.

Furthermore, although the third infusion line Z shown in FIG. 6 has the same configuration as the second infusion line Y, it may have a configuration different from the second infusion line Y.

The connection between the third infusion line Z and the first female connector end 32 of the first connector 30 is the same as that between the second infusion line Y and the first female connector end 32 of the first connector 30; therefore, it will not be described in detail.

The second infusion line Y and the third infusion line Z, as described above, are connected to the first infusion line X by two of the first connectors 30.

For the purposes of discrimination and clarity in illustration, the first connector 30 for connecting the second infusion line Y, distinguished from the first connector 30 for connecting the third infusion line Z, will be hereinafter called "first connector 30Y," and the parts of the first connector 30Y will be given a "Y" following their reference signs. Likewise, the first connector 30 for connecting the third infusion line Z will be hereinafter called "first connector 30Z," and the parts of the first connector 30Z will be given a "Z" following their reference signs. With that said, where there is no need to distinguish between the first connector 30Y and the first connector 30Z or where such discrimination is not required in description, the term "first connector 30" will be used as it has been used throughout the specification.

As shown in FIG. 7, a first partition 35Y of the first connector 30Y extends from the interior of a male connector end 31Y to the interior of a second female connector end 33Y.

More specifically, the first partition 35Y of the first connector 30Y includes a tip receiver 36Y that receives the tip of a male connector end 31Z of the first connector 30Z when the male connector end 31Z of the first connector 30Z is inserted into the second female connector end 33Y; and a protrusion 37Y that protrudes toward the tip 33Ya of the second female connector end 33Y with respect to the tip receiver 36Y. When the tip receiver 36Y receives the tip 31Za of the male connector end 31Z of the first connector 30Z, the protrusion 37Y is inside the male connector end 31Z of the first connector 30Z, thereby contiguously abutting against a first partition 35Z of the first connector 30Z.

Consequently, when the male connector end 31Z is inserted into the second female connector end 33Y, a tip end face at the tip 31Za of the male connector end 31Z abuts against the tip receiver 36Y of the first partition 35Y, whereby an insertion depth of the male connector end 31Z with respect to the second female connector end 33Y is restrained. More specifically, a clearance is defined between the protrusion 37Y and an inner peripheral surface of the second female connector end 33Y; when the male connector end 31Z is inserted into the second female connector end 33Y, a peripheral wall at the tip 31Za of the male connector end 31Z enters this clearance, and the tip end face of the male connector end 31Z abuts against the tip receiver 36Y of the first partition 35Y. In other words, the tip receiver 36Y, the protrusion 37Y, and the inner peripheral surface of the second female connector end 33Y together define a recess, where the tip receiver 36Y serves as a bottom. When the peripheral wall at the tip 31Za of the male connector end 31Z enters this recess and the tip end face of the male connector end 31Z abuts against the tip receiver 36Y, the male connector end 31Z is blocked from being further advanced in the second female connector end 33Y.

The recess, i.e., the above-described clearance, has a width from the protrusion 37Y of the first partition 35Y to the inner peripheral surface of the second female connector end 33Y, which width is substantially equal to or slightly smaller than the thickness of the peripheral wall at the tip 31Za of the male connector end 31Z. Thus, when the tip end face of the male connector end 31Z abuts against the tip receiver 36Y, an inner surface and an outer surface of the peripheral wall at the tip 31Za of the male connector end 31Z are in contact with a side surface of the protrusion 37Y of the first partition 35Y and the inner peripheral surface of the second female connector end 33Y, respectively, that is to say, the peripheral wall at the tip 31Za of the male connector end 31Z is disposed between the side surface of the protrusion 37Y of the first partition 35Y and the inner peripheral surface of the second female connector end 33Y.

Furthermore, when the tip end face of the male connector end 31Z abuts against the tip receiver 36Y, the protrusion 37Y of the first partition 35Y is inside the male connector end 31Z through an opening at the tip 31Za of the male connector end 31Z, and a tip end face of the protrusion 37Y abuts against a tip end face of the first partition 35Z in the male connector end 31Z. Here, when the tip end face of the male connector end 31Z abuts against the tip receiver 36Y, the entire tip end face of the protrusion 37Y abuts against the entire tip end face of the first partition 35Z.

In this way, when the male connector end 31Z of the first connector 30Z is inserted into the second female connector end 33Y of the first connector 30Y, the first partition 35Y of the first connector 30Y adjoins the first partition 35Z of the first connector 30Z so that the first partition 35Y and the first partition 35Z form a combined partition. With the combined partition formed, an in-flow channel 34aY of the first connector 30Y is in communication with an in-flow channel 34aZ of the first connector 30Z, and an out-flow channel 34bY of the first connector 30Y is in communication with an out-flow channel 34bZ of the first connector 30Z.

Furthermore, as shown in FIG. 7, when the second connector 14, the first connector 30Y, and the first connector 30Z are coupled to each other, the second partition 69, the first partition 35Y, and the first partition 35Z adjoin contiguously, forming a combined partition. Consequently, when the second connector 14, the first connector 30Y, and the first connector 30Z are interconnected, the liquid from the infusion bag P1 connected at the proximal end of the first infusion line X (see FIG. 6) flows through an upstream flow channel 64a of the second connector 14, the in-flow channel 34aY of the first connector 30Y, the in-flow channel 34aZ of the first connector 30Z, a connecting channel 34cZ of the first connector 30Z, the out-flow channel 34bZ of the first connector 30Z, the out-flow channel 34bY of the first connector 30Y, and a downstream flow channel 64b of the second connector 14, in the described order (see the arrows in FIG. 7).

In other words, by attaching the third infusion line Z to the entire infusion line shown in FIG. 2 by means of the first connector 30Z, the main route for the liquid from the infusion bag P1 can be extended from the interior of the first connector 30Y to the interior of the first connector 30Z through the second female connector end 33Y of the first connector 30Y. The liquid from the infusion bag P3 (see FIG. 6) merges with the main route at a first female connector end 32Z of the first connector 30Z, to which the distal end of the third infusion line Z has been connected.

Thus, the first connectors 30Y and 30Z according to the embodiment enable the main route, through which the liquid flows from the infusion bag P1 connected at the proximal end of the first infusion line X (see FIG. 6), to be extended to the interiors of the first connectors 30Y and 30Z. Consequently, the liquids from the additional infusion lines (the second infusion line Y and the third infusion line Z, in this embodiment) (the liquids from the infusion bags P2 and P3, in this embodiment) can merge with the main route, not in the second connector 14, but in the first connectors 30Y and 30Z to which the respective additional infusion lines are connected.

Accordingly, even though a plurality of additional infusion lines are attached to the first infusion line X, there are little differences between routes (i.e., subsidiary routes) to the points to merge with the main route regardless of the positions of the additional infusion lines. As a result, even though a dose per unit time of the liquid (s) from the additional infusion line(s) is smaller than a dose per unit time of the liquid from the infusion bag P1 in the first infusion line X, for example, as small as 1 mL to 5 mL per hour, the liquid(s) from the additional infusion line(s) can merge with the main route, or can be administered to the patient within a shorter period of time compared to a configuration in which the liquid(s) from the additional infusion line(s) merges with the main route in the second connector 14.

Although FIGS. 6 and 7 illustrate connection by two of the first connectors 30Y and 30Z, three or more of the first connectors 30 may be used to attach three or more additional infusion lines in the same way as described above. In that case also, there are few differences between the subsidiary routes regardless of the positions of the additional infusion lines, that is to say, there are few difference between the subsidiary routes despite the coupling of the first connectors 30.

[Cap 40]

Details of the cap 40 will now be described in relation to priming for the additional infusion line that is performed in the course of setting up the infusion lines shown in FIGS. 2 and 6. Here, priming for the second infusion line Y shown in FIG. 1 is taken by way of example in order to describe the cap 40 in detail.

As shown in FIG. 1, the infusion set including the first connector 30 and the second infusion line set 20 that forms the second infusion line Y that is connected to the first female connector end 32 of the first connector 30 is prepared; the cap 40 is used to perform priming for this infusion set.

Figure 8A:
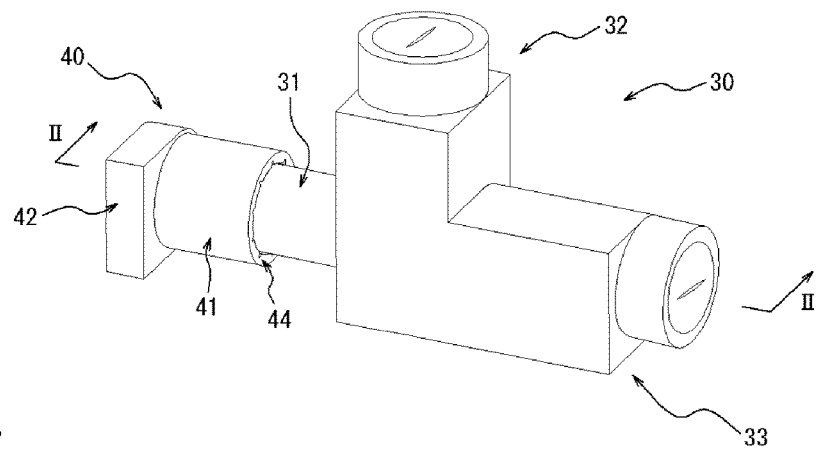
FIG. 8A is a perspective view showing a state in which a cap is attached to a male connector end.
Figure 8B:
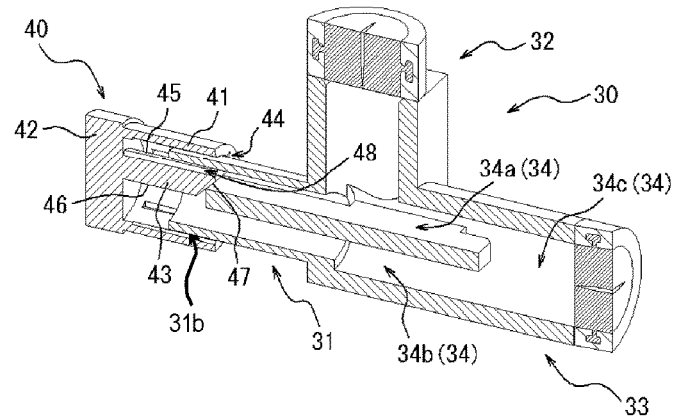
FIG. 8B is a cross-sectional perspective view taken along the II-II section in FIG. 8A.
Figure 8C:
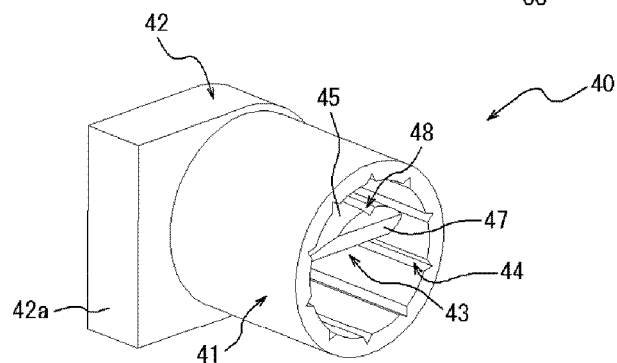
FIG. 8C is a perspective view showing the cap alone.

As shown in FIG. 1, the cap 40 is fit over the tip 31a of the male connector end 31 of the first connector 30. FIG. 8A is a perspective view showing a state in which the cap 40 has been attached to the male connector end 31 of the first connector 30; FIG. 8B is a cross-sectional perspective view taken along the II-II section in FIG. 8A. FIG. 8C is a perspective view showing the cap 40 alone.

First, the configuration of the cap 40 itself will be described. As shown in FIG. 8C, the cap 40 includes a cylinder 41 having a central axis; a top wall 42 formed integrally to the cylinder 41 at one end so as to close the cylinder 41 at the end; and a protrusion 43 protruding from the top wall 42 into the interior of the cylinder 41 along the central axis. The top wall 42 is provided with a lug 42a that is protruded radially externally from the cylinder 41.

As shown in FIG. 8C, an inner wall of the cylinder 41 is provided with elongated grooves 44 extending along the central axis, having substantially V-shape cross sections. The elongated grooves 44 are disposed around the circumference of the cylinder 41 at predetermined intervals from each other. Further, as shown in FIG. 8B, when the cap 40 is attached to the male connector end 31, a tip portion of the protrusion 43 is inside the in-flow channel 34a of the male connector end 31, being in contact with walls that define the in-flow channel 34a. As shown in FIGS. 8B and 8C, the protrusion 43 has side surfaces: a peripheral surface 45 that comes in contact with an inner peripheral surface of the male connector end 31 and a flat surface 46 that comes in contact with the first partition 35 and that is continuous with the peripheral surface 45. The tip portion of the protrusion 43 is provided with a planar slant surface 47 that is slanted with respect to and is continuous with the flat surface 46. The peripheral surface 45 is provided with an elongated groove 48 extending along the central axis of the cylinder 41, having a substantially V-shape cross section.

As shown in FIGS. 8A and 8B, the cap 40 is attached to the tip portion 31b of the male connector end 31 of the first connector 30 in such a manner that the cylinder 41 covers a periphery of the male connector end 31 and the top wall 42 covers the tip end face of the male connector end 31. The tip portion 31b of the male connector end 31 mates with the cap 40 with an outer peripheral surface of the male connector end 31 tightly held against an inner peripheral surface of the cylinder 41.

While the cap 40 is attached to the tip portion 31b of the male connector end 31 (see FIG. 8B), the cap 40 defines vent channels for blocking liquid communication between the interior and the exterior of the male connector end 31, yet allowing gas communication between the interior and the exterior of the male connector end 31. In FIG. 8B, gas communication between the interior and the exterior of the male connector end 31 is allowed by the elongated grooves 44 formed on the cylinder 41. More specifically, gas to be purged from the in-flow channel 34a of the male connector end 31 will pass through a cavity formed by the elongated groove 48 of the protrusion 43 and the inner peripheral surface of the male connector end 31, and then a cavity formed by the elongated groove 44 of the cylinder 41 and the outer peripheral surface of the male connector end 31 before being purged to the outside. Gas to be purged from the out-flow channel 34b of the male connector end 31 will pass through the cavity formed by the elongated groove 44 of the cylinder 41 and the outer peripheral surface of the male connector end 31 before being purged to the outside.

The cavity formed by the elongated groove 48 of the protrusion 43 and the inner peripheral surface of the male connector end 31 and the cavities formed by the elongated grooves 44 of the cylinder 41 and the outer peripheral surface of the male connector end 31 have cross-sectional areas that are so small that a fluid is not allowed to pass therethrough unless it is highly pressured. Thus, the cavity formed by the elongated groove 48 of the protrusion 43 and the inner peripheral surface of the male connector end 31 and the cavities formed by the elongated grooves 44 of the cylinder 41 and the outer peripheral surface of the male connector end 31 form the vent channels that block liquid communication between the interior and the exterior of the male connector end 31, yet allow gas communication between the interior and the exterior of the male connector end 31.

Because the cap 40 defines the vent channels while it is attached to the tip portion 31b of the male connector end 31, gas in the flow channel of the second infusion line Y can be purged through the vent channels, while the flow channel of the second infusion line Y is filled with a liquid such as medicinal fluid.

When the cap 40 according to the embodiment is attached to the tip portion 31b of the male connector end 31, the protrusion 43 of the cap 40 is inside the in-flow channel 34a through the opening at the tip 31a of the male connector end 31 so as to plug one end of the in-flow channel 34a that is in communication with the first female connector end 32. It follows that, when the second infusion line Y is primed, a liquid entering the first connector 30 via the first female connector end 32 fills the in-flow channel 34a, flows to the connecting channel 34c at the other end of the in-flow channel 34a, and then flows into the out-flow channel 34b. If the protrusion 43 is absent, the liquid entering the first connector 30 via the first female connector end 32 can flow into the out-flow channel 34b at both ends of the in-flow channel 34a, which may cause gas to remain in the out-flow channel 34b. Because the cap 40 according to the embodiment has the above-described protrusion 43, the first connector 30 can be more reliably filled with liquid upon priming.

Although the protrusion 43 of the cap 40 according to the embodiment plugs one end of the in-flow channel 34a, the protrusion 43 may plug either flow channel that directly communicates with the first female connector end 32; for example, if the out-flow channel 34b directly communicates with the first female connector end 32, the protrusion 43 can plug one end of the out-flow channel 34b.

The infusion set and the connector of the present invention are not limited to the specific configurations described in the above embodiments, but various modifications can be made without departing from the scope defined by the claims. For example, although the partition 35 of the first connector 30 and the partition 69 of the second connector 14 are contiguously abutted against each other to form a combined partition in the embodiments shown in FIGS. 3 and 7, the combined partition may have a slight gap between the partition 35 of the first connector 30 and the partition 69 of the second connector 14, as long as the flow through the main route including the in-flow channel 34a and the out-flow channel 34b of the first connector 30 is established. Likewise, although the partitions 35 of the first connectors 30 are contiguously abutted against each other to form a combined partition when the first connectors 30 are interconnected in the embodiment shown in FIG. 7, the combined partition may have a slight gap between the partitions 35 of the first connectors 30, as long as the flow through the main route including all of the in-flow channels 34a and the out-flow channels 34b of the interconnected first connectors 30 is established. Hence, the terms "contiguous," "adjoin," and the like used herein in contexts such as "the partition 35 of the first connector 30 and the partition 69 of the second connector 14" or "the partitions 35 of the first connectors 30" are "contiguous" or "adjoin (each other)" do not strictly mean that they abut against each other.

INDUSTRIAL APPLICABILITY

The invention relates to an infusion set and a connector.

What is claimed is:

1. An infusion set comprising:
a first infusion line set that forms a first infusion line with an injection port; and
a connector defining a flow channel and comprising:
    a male connector end that is insertable into the injection port,
    a first female connector end to which a second infusion line is connectable,
    a second female connector end, and
    a partition that extends into the male connector end and divides a portion of the flow channel into an in-flow channel and an out-flow channel,
wherein the injection port and the connector are configured such that, when the male connector end of the connector is inserted into the injection port, liquid is flowable from the injection port to the in-flow channel, from the in-flow channel around the partition to the out-flow channel, and from the out-flow channel back to the injection port,
wherein the male connector end has a first central axis, the first female connector end has a second central axis, and the second female connector end has a third central axis, the first central axis being substantially in line with the third central axis and intersecting the second central axis,
wherein the partition extends from an interior of the male connector end to an interior of the second female connector end, and
wherein the connector is configured such that, when a male connector end of an additional connector that is identical to the connector is inserted into the second female connector end, the partition adjoins a partition of the additional connector.

2. The infusion set according to claim 1, wherein:
the partition of the connector comprises a tip receiver and a protrusion that protrudes toward a tip of the second female connector end with respect to the tip receiver,
the connector is configured such that, when the male connector end of the additional connector is inserted into the second female connector end, the tip receiver receives a tip of the male connector end of the additional connector and the protrusion is inside the male connector end of the additional connector in such a manner that the protrusion adjoins the partition of the additional connector.

3. The infusion set according to claim 1, further comprising:
a cap configured to be attached to a tip portion of the male connector end, the cap defining vent channels configured to (i) block liquid communication between the interior and an exterior of the male connector end, but (ii) allow gas communication between the interior and the exterior of the male connector end,
wherein the cap has a protrusion configured to enter the male connector end through an opening at a tip of the male connector end and plug into one of the in-flow channel and the out-flow channel that is in communication with the first female connector end when the cap is attached to the tip portion of the male connector.

4. A connector configured to be connected to an injection port disposed in a first infusion line, the connector defining a flow channel and comprising:
a male connector end that is insertable into the injection port;
a first female connector end to which a second infusion line is connectable;
a second female connector end into which a male connector end of an additional connector that is identical to the connector is insertable; and
a partition that extends into the male connector end and divides a portion of the flow channel into an in-flow channel and an out-flow channel,
wherein the connector is configured such that, when the male connector end is inserted into the injection port, liquid is flowable from the injection port to the in-flow channel, from the in-flow channel around the partition to the out-flow channel, and from the out-flow channel back to the injection port, and
wherein the connector is configured such that, when the male connector end of the additional connector is inserted into the second female connector end, the partition adjoins a partition of the additional connector.

5. An infusion set comprising:
the connector according to claim 4; and
a second infusion line set that forms the second infusion line that is connectable to the first female connector end.

6. A combination comprising:
a first connector defining a first flow channel and comprising:
   a male connector end,
   a first female connector end, and
   a first partition that extends into an interior of the male connector and divides a portion of the first flow channel into an in-flow channel and an out-flow channel;
a second connector defining a second flow channel and comprising:
   an upstream port to which a proximal portion of a first infusion line is connectable;
   a downstream port to which a distal portion of the first infusion line is connectable,
   a second female connector end into which the male connector end of the first connector is insertable, and
   a second partition that extends into an interior of the second female connector end and divides a portion of the second flow channel into an upstream flow channel and a downstream flow channel;
wherein the first connector and the second connector are configured such that, when the male connector end of the first connector is inserted into the second female connector end of the second connector, the first partition cooperates with the second partition such that liquid is flowable from the upstream port to the upstream flow channel of the second connector, from the upstream flow channel of the second connector to the in-flow channel of the first connector, from the in-flow channel around the first partition to the out-flow channel of the first connector, from the out-flow channel of the first connector to the downstream flow channel of the second connector, and from the downstream flow channel to the downstream port of the second connector.

7. The combination of claim 6, wherein:
the second partition comprises:
   a tip receiver configured to receive a tip of the male connector end of the first connector when the male connector end of the first connector is inserted into the second female connector end of the second connector, and
   a protrusion that protrudes towards a tip of the second female connector end with respect to the tip receiver; and
the first connector is configured such that, when the tip receiver receives the tip of the male connector end of the first connector, the protrusion is located inside the male connector end of the first connector and abuts the first partition of the first connector.

* * * * *